United States Patent [19]
Acker

[11] Patent Number: 5,928,248
[45] Date of Patent: Jul. 27, 1999

[54] GUIDED DEPLOYMENT OF STENTS

[75] Inventor: David E. Acker, Setauket, N.Y.

[73] Assignee: Biosense, Inc., New Brunswick, N.J.

[21] Appl. No.: 09/030,407

[22] Filed: Feb. 25, 1998

Related U.S. Application Data

[63] Continuation-in-part of application No. PCT/US97/02335, Feb. 14, 1997
[60] Provisional application No. 60/038,498, Feb. 25, 1997.

[51] Int. Cl.⁶ .................................................... A61F 11/00
[52] U.S. Cl. ........................... 606/108; 128/898; 600/424
[58] Field of Search ..................................... 606/108, 191, 606/194, 192, 198; 128/898; 600/424; 607/122

[56] References Cited

U.S. PATENT DOCUMENTS

| | | |
|---|---|---|
| 5,042,486 | 8/1991 | Pfeiler et al. ............................ 600/424 |
| 5,391,199 | 2/1995 | Ben-Haim ................................ 607/122 |
| 5,840,025 | 11/1998 | Ben-Haim ................................ 600/424 |

*Primary Examiner*—Michael Buiz
*Assistant Examiner*—Kevin Truong
*Attorney, Agent, or Firm*—Paul A. Coletti

[57] ABSTRACT

A stent is placed in a tubular structure of the anatomy such as the vascular or respiratory system by advancing a probe bearing the stent into the body. The disposition of the probe, and hence the disposition of the stent are monitored using a system which transmits non-ionizing fields between a transducer or transducers on the probe and external transducers. The disposition of the stent relative to the tubular structure is depicted showing a representation of the stent superposed on an image of the tubular structure. This provides accurate placement, particularly for complex stents with features such as one or more branches which must be aligned with anatomical features.

13 Claims, 3 Drawing Sheets

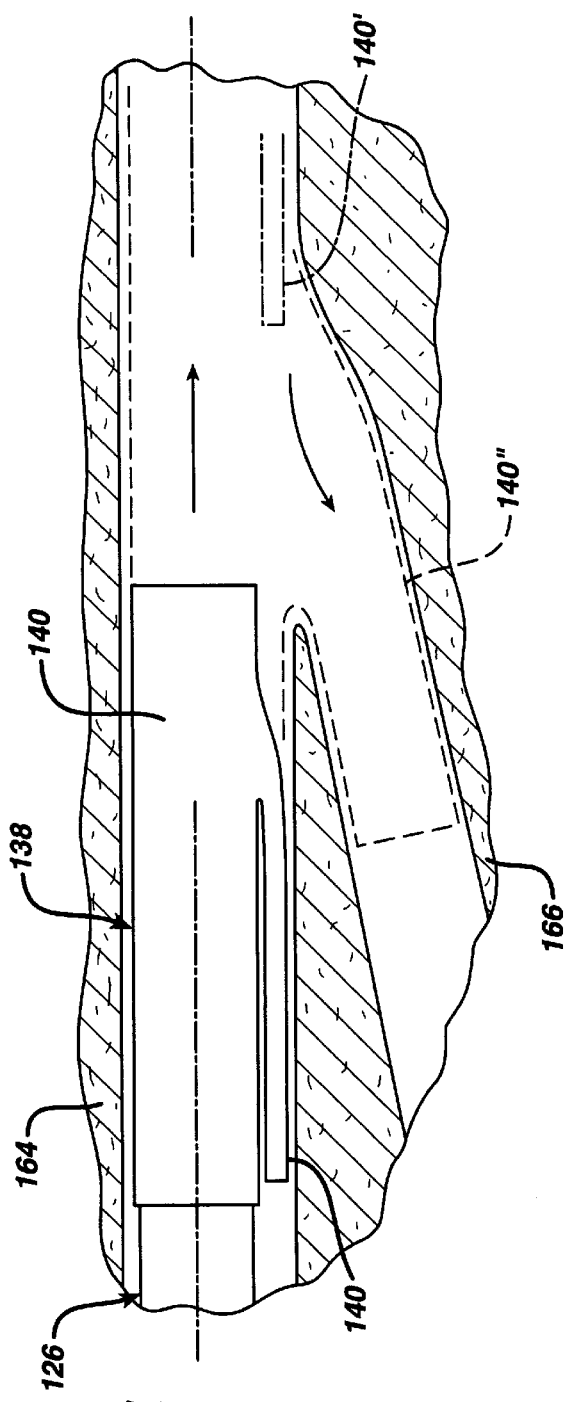
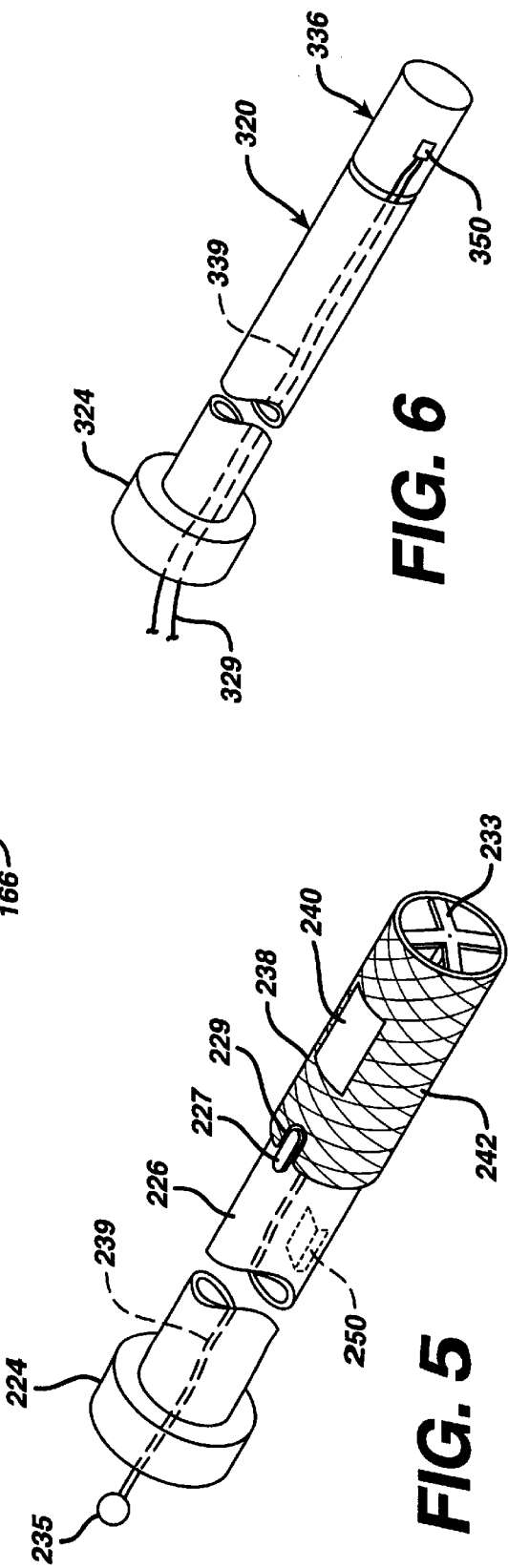

GUIDED DEPLOYMENT OF STENTS

CROSS REFERENCE TO RELATED APPLICATIONS

The present application claims benefit of U.S. Provisional Patent Application 60/038,498, filed Feb. 25, 1997, the disclosure of which is hereby incorporated by reference herein. The present application is also a continuation-in-part of PCT International Application PCT/US97/02335, filed Feb. 14, 1997, the disclosure of which is also incorporated by reference herein.

BACKGROUND OF THE INVENTION

The present invention relates to placement of stents within tubular structures of the body such as the veins or arteries of the vascular system; the airways of the respiratory system; and the passages of the intestinal tract. As referred to in this disclosure, stents are structures which are placed within tubular structures of the body so as to reinforce or line the tubular structure. For example, a stent may be placed within an artery to maintain patency of the artery after angioplasty or to reinforce the arterial wall as, for example, if an aneurysm is present. Also, stents may be placed within the esophagus or within an airway to keep the airway or esophagus open in the presence of a tumor or other abnormal growth. Stents can be placed within the body using a elongated probe such as a catheter or endoscope. The stent is held on the distal end of the probe. The stent typically is retained on the probe by a holding device such as a balloon which can be operated from the proximal end of the probe. The physician advances the probe into the tubular structure, distal end first, until the distal end of the probe is positioned at the appropriate location within the tubular structure. When the distal end of the probe is appropriately positioned, the physician actuates the holding device to release the stent. For example, in the case of a balloon actuated stent, the physician may momentarily inflate the balloon so as to expand the stent into engagement with the tubular structure and then deflate the balloon so as to release the stent from the probe.

Procedures of this nature typically have been performed using fluoroscopic or other images acquired during the procedure. Fluoroscopic imaging exposes both the patient and the physician to radiation. Moreover, many internal tubular structures such as arteries are not readily visualized using fluoroscopic imaging unless contrast media are employed. These add to the complexity of the procedure and, in some cases, present some additional risk to the patient. If the procedure is performed using tomographic x-ray imaging (commonly referred to "CT" or "CAT") or magnetic resonance imaging (MRI) during the procedures, the apparatus is occupied for the entire time required to perform the procedure. The need for such apparatus during the procedure adds to the cost of the procedure and limits the locations where the procedure can be performed. Other procedures for placement of stents have been guided by direct visual observation of the body by means of optical systems included in an endoscope used to place the stent. These techniques are best applied in relatively large structures.

Certain stents have been developed for reinforcing tubular structures which include branching elements as, for example, the Y-shaped intersections of arteries or the Y-shaped intersection of the trachea and the primary bronchi. These stents include a first reinforcing element having one longitudinal axis and one or more branch or secondary reinforcing elements having longitudinal axes transverse to the longitudinal axis of the first element. For example, in reinforcing a generally Y-shaped section of a branching arterial network, the stent used is also generally Y-shaped. Positioning of branching stents poses additional problems. Thus, in placing an ordinary stent, with only a single tubular structure having uniform properties around its longitudinal axis, there is no need to control the orientation of the stent in roll or rotation around the longitudinal axis. Although the longitudinal axis of the stent must be reasonably well-aligned with the longitudinal axis of the tubular structure, this alignment typically is maintained by the mechanical engagement of the stent or probe in the tubular structure itself. However, when a branching stent is installed in a branching structure, the orientation of the branching stent must be matched to the orientation of the branching structure. For example, is a generally Y-shaped stent is to be installed in a generally Y-shaped branching structure, the orientation of the stent must be controlled so that the branches point in the correct directions to fit within the branches of the artery, airway or other tubular structure. Thus, many procedures for placing such stents involve careful threading of guide wires through the branching structure to guide deployment of the shunt. Other types of stents may also require control of orientation.

Other medical procedures have been performed heretofore using position-monitoring equipment in which a magnetic, electromagnetic or other non-ionizing field is transmitted to or from the probe. As described, for example, in U.S. Pat. Nos. 5,558,091, 5,391,199; 5,443,489; and in PCT International Publication WO 96/05768, the disclosures of which are hereby incorporated by reference herein, the position, orientation or both of the distal end of a probe used for procedures such as surgery, cardiac monitoring or cardiac ablation can be determined by using one or more field transducers such as a Hall effect or magnetoresistive device, coil or other antenna carried on the probe, typically at or adjacent the distal end of the probe. One or more additional field transducers are disposed outside the body in an external frame of reference. The field transducers preferably are arranged to detect or transmit non-ionizing fields or field components such as a magnetic field, electromagnetic radiation or acoustical energy such as ultrasonic vibration. By transmitting the field between the external field transducers and the field transducers on the probe, characteristics of field transmission between these devices can be determined. The position and/or orientation of the sensor in the external frame of reference can then be deduced from these transmission characteristics. Because the field transducer of the probe allows determination of the position of the probe, such transducer is also referred to as a "position sensor".

As described, for example, in the aforementioned U.S. Pat. No. 5,558,091, the frame of reference of the external field transducers can be registered with the frame of reference of imaging data such as magnetic resonance imaging data, computerized axial tomographic data, or conventional x-ray image data and hence the position and orientation data derived from the system can be displayed as a representation of the probe superimposed on an image of the patient's body. The physician can use this information to guide the probe to the desired location within the patient's body, and to monitor its orientation during treatment or measurement of the body structure. This arrangement greatly enhances the ability of the physician to navigate the distal end of the probe through bodily structures. The transducer-based system avoids the difficulties associated with navigation of a probe by continuous imaging of the probe and patient during the procedure. For example, it avoids exposure to ionizing radiation inherent in fluoroscopic systems.

SUMMARY OF THE INVENTION

One aspect of the present invention includes methods of applying stents in tubular structures within the body of a patient. A method according to this aspect of the present invention desirably includes the steps of advancing a probe bearing a stent into the tubular structure of the body and determining the disposition of the stent relative to the patient by a procedure which includes the steps of transmitting one or more non-ionizing fields to or from at least one field transducer on the probe or on the stent, detecting each such transmitted field and deducing the disposition of the field transducer at least partially from the properties of the detected fields. Because the field transducer on the probe or stent passes into the patient's body, it is referred to herein as the "internal" field transducer. Methods according to this aspect of the present invention desirably further include the step of releasing the stent from the probe when the determining step indicates that the stent is at a disposition such that the released stent will be disposed on a preselected region of the tubular structure which requires stenting. The term "disposition" as used in the present disclosure, refers to the position, orientation or both of an object. Most preferably, the disposition-determining step is performed so that both the position and orientation of the stent are determined, and the stent is released only when it is in a predetermined orientation relative to the patient. Typically, the tubular structure includes a primary tube such as an artery, airway or other element having a longitudinal axis. The disposition-determining step desirably is performed so that the orientation of the step in roll about the longitudinal axis of the tubular element is determined. The tubular structure may be a branching structure including one or more branches intersecting the primary tube. The stent may include a first reinforcing element adapted to fit within the primary tube structure and one or more secondary or branch reinforcing elements adapted to fit within the branches. In this case, the method desirably further includes the step of adjusting the orientation of the stent on the basis of the disposition found in the disposition determining step so that the first or primary reinforcing element is disposed in the primary tube, whereas the branch reinforcing elements are disposed in the branches f the tubular structure. For example, where the tubular structure is a Y-shaped branching structure, and includes a primary tube constituting the base of the Y and two branches constituting the arms of the Y, the stent includes a similar Y-shaped structure.

The step of determining the position of the stent relative to the patient preferably includes the step of superposing a representation of the stent or the probe on an image of the patient. Preferably, the image of the patient includes depictions of the tubular structure in which the stent is to be placed. The step of transmitting one or more non-ionizing fields to or from the internal field transducer on the probe or stent desirably includes the step of transmitting such fields between each such internal field transducer and one or more locating field transducers having known disposition relative to one another and defining a locating frame of reference. The disposition of the internal field transducer, and hence the disposition of the stent, is found by monitoring transmitted fields. This disposition in the locating frame of reference can be transformed into a common frame of reference with the image of the patient. For example, the disposition of the stent can be transferred into the frame of reference of an image, such as a previously acquired MRI, CT or other image of the patient.

A further aspect of the present invention provides apparatus for positioning a stent. Apparatus according to this aspect of the invention includes an elongated probe having proximal and distal ends. The distal end of the probe is adapted for insertion within a tubular structure of a patient's anatomy. The apparatus further includes a stent releasably positioned on the probe adjacent the distal end thereof and at least one field transducer mounted on the stent or on the probe adjacent the distal end of the probe. The probe also includes one or more signal transmission paths extending from the field transducer towards the proximal end of the probe. Apparatus according to this aspect of the present invention may be utilized in methods is discussed above. Preferably, the stent includes at least one primary reinforcing element and at least one branch reinforcing element, the reinforcing structures having axes which intersect one another and which typically are oblique to one another. A portion of the probe adjacent the distal end thereof desirably has an axis of elongation and the axis of the first reinforcing structure may be aligned with such axis of elongation.

Preferably, the field transducer is mounted on the probe adjacent the distal end and the stent is releasably mounted on the probe so that the orientation of the stent relative to the probe remains substantially fixed while the stent is engaged with the probe. Thus, the orientation of the stent bears a fixed relation to the orientation of the field transducer on the probe. The probe desirably includes one or more engaging elements movably mounted on the probe adjacent the distal end thereof, and an actuator disposed at or near the proximal end of the probe, the actuator being linked to the engaging element so that the engaging element can be moved by the actuator to release the stent from the probe. For example, the engaging element may be a balloon defining an interior space and at least one reinforcing element of the stent may be a tubular element surrounding the balloon. The actuator may be a fluid connector and the actuator may be connected to the engaging element or balloon by a tube extending longitudinally along the probe.

These and other objects, features and advantages of the present invention will be more readily apparent from the detailed description set forth below, taken in conjunction with the accompanying drawings.

BRIEF DESCRIPTION OF THE DRAWINGS

FIG. 4 is a diagrammatic sectional view depicting portions of apparatus according to a further embodiment of the invention.

FIG. 5 is a perspective view depicting apparatus according to yet another embodiment.

FIG. 6 is a perspective view depicting apparatus according to a further embodiment of the invention.

DETAILED DESCRIPTION OF THE PREFERRED EMBODIMENTS

Figure 1:
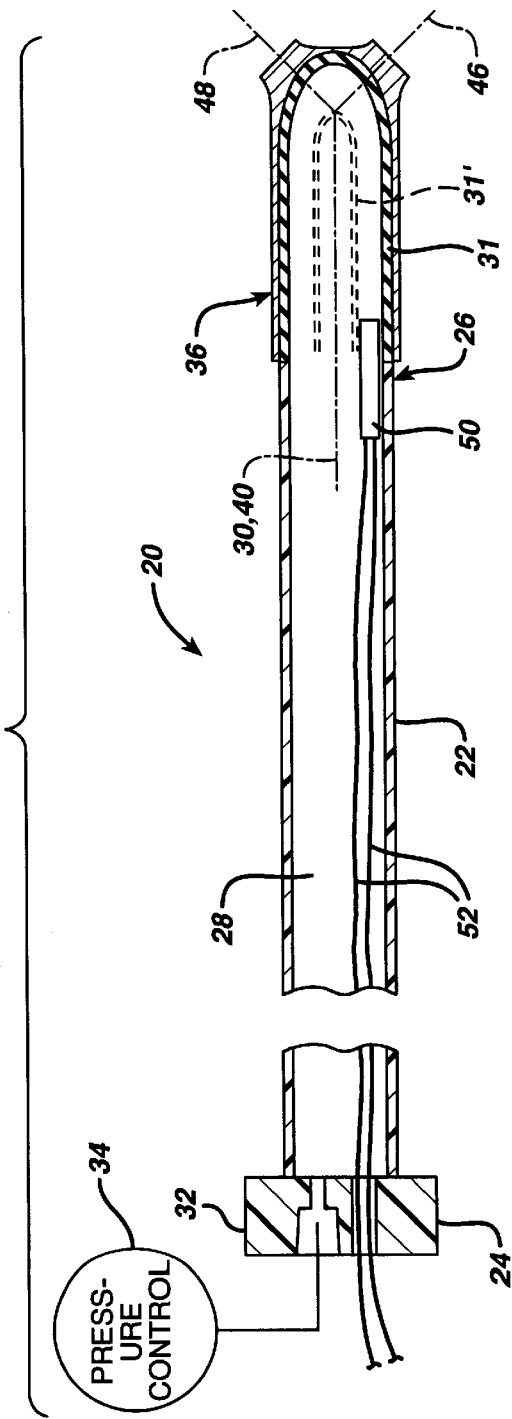
FIG. 1 is a diagrammatic partially sectional view depicting apparatus in accordance with one embodiment of the invention.

Apparatus according to one embodiment of the present invention includes a probe 20. Probe 20 desirably includes a catheter having an elongated tubular body 22. Body 22 has a handle portion or hub 24 affixed to a proximal end of the body and has a distal portion 26 remote from handle 24. Body 22 has a bore 28 extending longitudinally from its proximal end to its distal end and handle 24. Body 22 may incorporate a flexible section adjacent the distal end, so that the distal end 26 can be bent or pivoted relative to the remainder of the body. The catheter may incorporate devices (not shown) for bending the distal end of the body so as to steer the device as it is advanced into the patient's anatomy. The distal end of the catheter body defines a probe body axis 30.

A movable element in the form of a balloon 31 is mounted on the distal end 26 of the catheter body. Balloon 31 is movable between the moderately inflated position depicted in solid lines in FIG. 1, the deflated position 31' shown in broken lines, and a fully inflated position (not shown) wherein the balloon is expanded beyond the partially inflated position. Handle 24 is provided with a fitting 32 such as a threaded fitting or standard luer taper fitting communicating with bore 28. Bore 28 communicates with the interior of balloon 31. Thus, balloon 31 can be moved between the inflated position 31 and the deflated position 31' by releasing fluid from bore 28 through fitting 32. Fitting 32 may be connected to a pressure control device 34 arranged to admit or release fluid from the bore. The pressure control device may be a manual device such as a syringe, bulb or bellows, or any other fluid-admitting or withdrawing device which can be selectively actuated.

A stent 36 is releasably positioned on movable element or balloon 31 and is held in engagement with the distal end of the probe by the balloon when the balloon is in the inflated position as illustrated in solid lines. Stent 36 is a self-expanding device formed from a screen or mesh of so-called shape-memory alloy wire such as that sold under the trademark NITINOL and other alloys. The stent stably maintains the configuration shown in solid lines in FIG. 2 while the stent is at a temperature well below normal body temperature, preferably below about 30° C. The shape memory alloy changes configuration spontaneously when its temperature is elevated to normal body temperature, i.e., about 37° C., so that the stent spontaneously changes shape and spontaneously assumes the expanded configuration depicted in broken lines in FIG. 2. It is to be understood, of course, that other embodiments of stents are intended to be encompassed herein, such as balloon expandable or permanently deformable stents sold, such as those sold under the tradename PALMAZ-SCHATZ, and marketed by Cordis Corporation, Miami Lakes Fla., a sister company of the assignee of the present invention.

The stent includes a primary tubular reinforcing element 38 having an axis 40 and a pair of tubular branch elements 42 and 44 having axes 46 and 48 respectively. The branch elements intersect the primary tubular element 38 at the distal end of such element so that the structure as a hole is generally Y-shaped. The axes 46 and 48 of the branch tubular elements and the axis 40 of the primary tubular element lie generally in a lane parallel to the plane of the drawing as seen in FIGS. 1 and 2.

Figure 2:
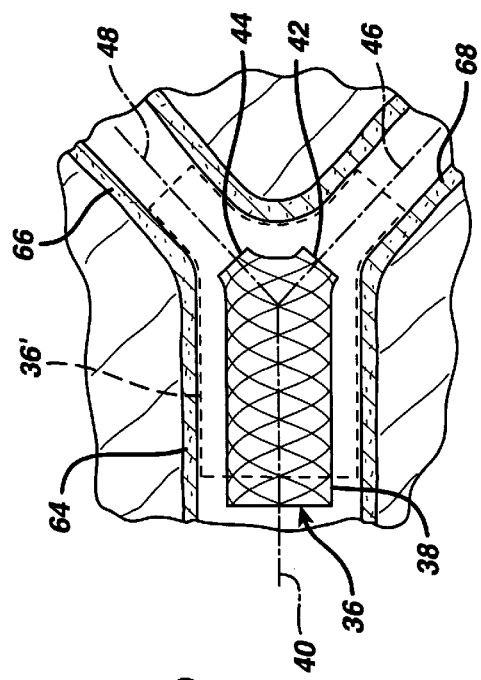
FIG. 2 is a diagrammatic sectional view on an enlarged scale, depicting a portion of the apparatus of FIG. 1 in conjunction with body structures of the invention.

When the stent is positioned on the catheter as shown in FIG. 1, the axis 40 of the primary tubular element 38 is aligned with the probe axis 30 defined by the distal end of the catheter. Balloon 31 bears on the interior or the stent and frictionally engages the stent. In this condition, the stent is firmly held on the movable element or balloon 31 so that the stent will not move with respect to the distal end of the catheter. In particular, the stent will not roll around axis 30.

A field transducer or position sensor 50 is mounted in probe body 22 adjacent the distal end 26 thereof. Transducer 50 may be a sensor arranged to detect magnetic or electromagnetic fields. For example, the sensor 50 may be a multiaxis, solid-state position sensor of the type disclosed in the aforementioned U.S. Pat. No. 5,558,091. Such a sensor incorporates a plurality of transducers sensitive to magnetic field components in mutually orthogonal directions. Other suitable position sensors include coils as disclosed in the aforementioned U.S. Pat. No. 5,391,199 and in PCT Application PCT/US95/01103, now published as PCT International Publication WO 96/05768, the disclosure of which is hereby incorporated herein by reference. Such coils may be provided as a single coil or as a plurality of orthogonal coils capable of detecting field components in orthogonal directions. Position sensor or field transducer 50 is connected to leads 52 which extend through bore 28 to and beyond the proximal end 24 of body 22.

The apparatus further includes a set of external field transducers or antennas 54 defining a locating frame of reference. For example, external field transducers 54 may be mounted to a patient-supporting bed 51. Antennas 54 are linked to a field transmitting and receiving device 56 and a computer 58, which in turn is linked to conventional input devices 59 such as a mouse or trackball and a keypad, and to a display device such as a cathode ray tube 60. These elements are arranged to cooperate with the field transducer 50 on the probe to determine the dispositions of the field transducers on the probes, and hence determine the dispositions of the distal end 26 of probe 20 in the frame of reference of the external field transducers or antennas 54. These elements of the apparatus can be as described in the aforementioned '091 or '199 patents. Other devices for detecting disposition of probes equipped with position sensors by transmission of non-ionizing fields are known in the art.

As is known in the art, electromagnetic or magnetic fields can be transmitted between an antenna or field transducer mounted in an external frame of reference and a field transducer on a probe, and the disposition of the probe can be calculated from the characteristics of the fields detected by the transducer on the probe. Thus, the external field transducers or antennas 54 and the position sensor or probe field transducer 50 on the probe cooperatively define a plurality of transmitter-receiver pairs. Each such pair includes one transmitter and one receiver as elements of the pair. One element of each such pair is disposed on the probe and the other element of each such pair is disposed at a known disposition in the external frame of reference. Typically, at least one element of each transmitter-receiver pair is disposed at a different position or orientation than the corresponding element of the other pairs. By detecting the characteristics of field transmission between elements of the various pairs, the system can deduce information concerning the disposition of the probe in the external frame of reference. The disposition information can include the position of the probe, the orientation of the probe or, most preferably, both position and orientation in all degrees of freedom.

Although the external field transducers 54 are illustrated as mounted to a rigid structure such as a patient bed, so that the external field transducers remain in fixed position relative to one another, this is not essential. As described in commonly assigned PCT Publication WO 97/29685, the disclosure of which is incorporated by reference herein, the external field transducers may be movable relative to one another. The computer system can determine the positions of the external field transducers by measuring the properties of fields transmitted between these transducers, or between the external field transducers and calibration transducers mounted to the individual external field transducers.

The apparatus further includes a fixture 70 mounted in a fixed or known disposition relative to external field transducers 54. Fixture 70 includes a pocket 72 having a shape adapted to fit stent 36 when the stent is in the unexpanded condition shown in FIG. 1. Pocket 72 lies in known position and orientation relative to external field transducers 54.

A plurality of fiducial markers 62 are also provided. Each marker 62 has properties which make it visible in the imaging modality which will be used to acquire an image of the patient's body. For example, where x-ray based imaging modalities will be used, the fiducial markers are radio-opaque. If magnetic resonance imaging is employed, the fiducial markers have magnetic resonance properties which are different from those of normal body tissues. Each fiducial marker 62 also includes a field transducer similar to the internal field transducer mounted on the probe. The field transducers incorporated in the fiducial markers are arranged to interact with the external field transducers 54, field transmitting and receiving device 56 and computer 58 in the same manner as discussed above with reference to the internal field transducer 50 on the probe. The computer can determine the disposition of the fiducial markers in the same way as it determines the disposition of the probe distal end.

Figure 3:
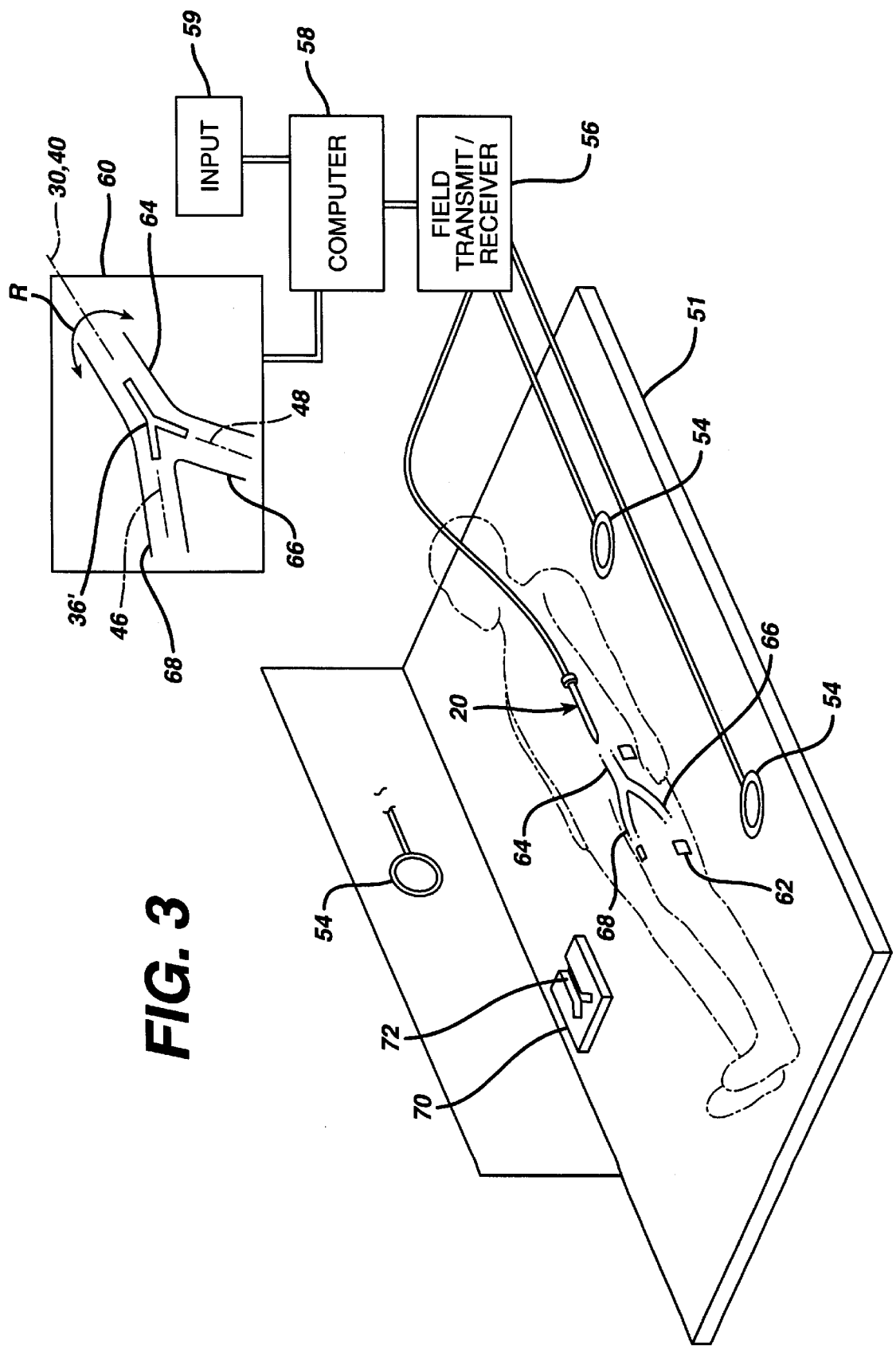
FIG. 3 is a diagrammatic perspective view depicting further elements usable with the apparatus of FIG. 1.

In a method according to an embodiment of the invention the fiducial markers are placed on the patient and an image of the patient is acquired by a conventional imaging modality as discussed above. The image encompasses a part of the patient's anatomy which includes a tubular structure which requires a stent. For example, as shown in FIG. 3, the image may include an arterial structure including a large, principal artery 64 joining two branch arteries 66 and 68 at a generally Y-shaped intersection. The image also includes the fiducial markers 62. The image is supplied as computer data, such as digital information specifying the radioopacity or magnetic resonance properties of individual volume elements of the patient. After imaging, the patient is positioned on bed 51.

Field transmitting and receiving apparatus 56 and computer 58 are actuated to determine the location of the fiducial markers 62 in the locating frame of reference defined by the external field transducers 54. Thus, the locations of the fiducial markers in the locating frame of reference are provided to the computer. An operator can input the locations of the fiducial markers in the frame of reference of the image. For example, computer 58 can be actuated to display depictions of the image which include the fiducial markers in two orthogonal planes and the operator can manually adjust cursors on these depictions by adjusting a knob, trackball or mouse incorporated in input unit 59 until the cursors are positioned over the depictions of a particular fiducial marker. Once the cursors are aligned with the depictions of the fiducial marker, the operator can provide a further indication, as by entering a command through input-output devices 59. This signals the computer that the coordinates of the cursor in the image frame of reference correspond to the coordinates of the fiducial marker. Once the coordinates of the fiducial markers have been provided to the computer in the image frame of reference and in the locating frame of reference in this manner, the computer can derive a mathematical transformation between the locating frame of reference and the image frame of reference.

Other techniques for acquiring locations of points in the imaged anatomy and deriving transformations between an image frame of reference and a locating frame of reference are well known and are described in the aforementioned patents and publications. In one such technique also described in these patents and publications, the patient is not provided with fiducial markers during the imaging step. Instead, a reference field transducer is manually aligned with several readily identifiable points in the anatomy which are included in the image. The position of each such identifiable point in the locating frame of reference is acquired by actuating the reference field transducer in conjunction with the external field transducers, in the same manner as described above. The operator can input the positions of the identifiable points in the anatomy in the same manner as discussed above, so that the computer has the positions of these points in both frames of reference. In other variants, the system acquires a succession of positions in the locating frame of reference while the reference field transducer is moved over a well-defined contour in the patient's anatomy. The computer system uses automatic pattern-matching techniques to find a feature having a contour including a set of locations in the image frame of reference which can be mapped to the set of locations in the locating frame of reference by a rigid-body transformation. Again, various techniques for finding matching points in both frames of reference, and for deriving a transformation between the locating and imaging frames of reference, are well known in the art.

Stent 38 is disposed on the distal end of the probe by balloon 31, so that the orientation of the stent is fixed with respect to the orientation of the field transducer 50. The relationship between the orientation of the stent and the orientation of the field transducer can be input into the computer system by bringing the stent to a known orientation in the locating frame of reference and actuating the computer system to register the orientation of the field transducer while the stent is in this known orientation. For example, the distal end of the probe, with the stent thereon, can be placed on fixture 70 so that the stent is received in pocket 72. In this condition, the stent lies at a known disposition in the locating frame of reference defined by transducers 54. The plane defined by axes 40, 46 and 48 of the tubular elements lies in the horizontal plane of the fixture, and the axes 30 and 40 of the probe distal end and primary tubular structure of the stent extend in a preselected direction defined by the fixture. Also, the position of the stent is fixed with respect to the locating frame of reference. While the probe and stent are in this known disposition, the computer acquires the orientation and position of the field transducer 50 on the probe. Using the same techniques as discussed above, the computer calculates a transform between the disposition of field transducer 50 and the orientation of the stent as, for example, a transformation between the orientation of field transducer 50 and the orientation of the plane of the tubular elements and axes 46, 48 and 40. Because the stent remains fixed with respect to the probe, this relationship between the orientation of the stent and the orientation of the field transducer on the probe will remain fixed during the procedure, until the stent is disposed into the vessel.

The physician then advances the distal end of the probe, with the stent thereon into the tubular structure of the patient's anatomy as, for example, into the primary tubular element or artery 64. During this procedure, the pressure control device is actuated to maintain a tight fit between the stent and balloon 31. If the stent begins to change configuration, the diameter of the primary reinforcing element 38 may increase slightly and the balloon will be correspondingly inflated to maintain tight engagement with the stent. The system continually acquires the location and orientation of internal field transducer 50 on the distal end of the probe. Using the known relationship between the disposition of the field transducer and the disposition of the stent, the system continually calculates the disposition of the stent, and transforms this known disposition into a disposition in the frame of reference of the image of the patient. The system continually displays a representation of the stent superimposed on the image at a disposition corresponding to the actual disposition of the stent in the image frame of reference.

This display is shown on cathode ray tube 60. The display thus shows the position and orientation of the stent relative to the surrounding portions of the patient's anatomy, including the surrounding portions of the tubular structure or arteries. For example, in the condition illustrated in FIGS. 2 and 3, stent 36 has been brought to a location at the intersection of primary artery 64 with branch arteries 66 and 68. Thus, a representation 36' of the stent is superposed on the depiction of the intersection. The representation 36' shows the generally Y-shaped configuration of stent 36. The orientations of axes 40, 46 and 48 are clearly shown in the correct orientation with respect to the arteries. By twisting the proximal end of the catheter body, the physician can adjust the orientation of the stent in roll around the axis 40 of the primary reinforcing element as indicated by arrow R. This aligns the axes 46 and 48 of the branch elements with the branch structures or arteries 66 and 68 in the patient's anatomy. The physician holds the stent in the correct position and orientation, while the stent changes configuration to the fully expanded condition 36' (FIG. 2). During this stage, the pressure control device maintains engagement of the balloon and stent.

When the stent is fully expanded, the physician can release it from the distal end of the catheter. The physician can actuate the pressure control device 34 (FIG. 1) to bring the balloon or movable element to its releasing or deflated position 31', whereupon the catheter may be withdrawn. Alternately, the physician can leave the balloon inflated to a fixed condition and allow the gradual change in the configuration of the stent to increase the diameter of the primary reinforcing element 38 and release the stent from the balloon.

In a further embodiment of the invention, the stent includes a primary reinforcing element 138 and a single branch reinforcing element 140. The branch reinforcing element is arranged to collapse or fold to the position illustrated in solid lines in FIG. 4. The stent is engaged with the distal end 126 of a probe and guided through a tubular structure such as a primary artery or vein 164 in an advancing direction until the branch reinforcing element is positioned at the opening of a branch 166 of the patient's tubular structure, such as a branch intersecting artery 164.

Here again, the orientation of the stent is displayed in registration with the image of the patient, so that the orientation of the stent around the axis 140 of the primary reinforcing element can be adjusted to align the branch reinforcing element 140 with branch structure 166. Once such alignment has been achieved, the probe and the stent are retracted slightly (to the left as seen in FIG. 4) so as to thread the collapsed branch reinforcing element 140 into branch structure or artery 166, whereupon the branch reinforcing element expands as illustrated at 140" in FIG. 4. The probe of FIG. 4 is equipped with a balloon (not shown) similar to the balloon 31 of the probe shown in FIG. 1. The balloon may be used to forcibly expand the primary reinforcing element 138 into engagement with the wall of the primary structure or artery 164. Here again, it is important to control the orientation of the stent during the placement procedure. The imaging and superposition procedure, which allows the physician to observe the disposition of the stent relative to the patient's anatomy is useful in this embodiment as well.

As shown in FIG. 5, a stent may include only a single tubular element 238. However, even with such a stent, it may be desirable to provide an indication of orientation of the stent during placement. For example, the stent may incorporate a patch 240 on only a portion of its surface. The patch 240 may be applied, for example, to cover an opening of an aneurysm or a fistula, leaving the remainder of the vessel wall covered only by a mesh framework 242 constituting the remainder of tubular element 238. Here again, the orientation and position of the stent relative to the patient's anatomy can be displayed as, for example, by superposing a representation of the stent on a depiction of the anatomy in the manner discussed above. The physician can align the patch 240 with the opening to be blocked.

In the structure of FIG. 5, the orientation of the stent relative to the distal end 226 of the probe body is fixed by a key 227 on the probe body engaging a slot 229 in the stent. Thus, the orientation of the stent relative to the field transducer 250 on the probe is known and there is no need to determine the relative orientations of these elements during use of the device, as by use of fixture 70 (FIG. 3).

Other arrangements for fixing the stent at a known orientation may be employed. For example, the distal end of the probe may have a non-circular cross section and the stent may have a corresponding noncircular cross section. Also, in the arrangement of FIG. 5, the stent is held on the distal end of the probe by a set of locking fingers 233 which are movably mounted on the distal end of the probe body. A mechanical linkage in the form of a cable 239 extending along the bore of the probe to the proximal end 224 connects fingers 233 with an actuating knob 235. The physician can release the stent by moving the actuating knob so as to swing fingers 233 into a collapsed or release position. The configuration of the movable elements used to retain the stent on the distal end of the probe may be varied. Also, other devices, such as other mechanical linkages, pneumatically actuated linkages or electrically operated devices at the distal end of the probe may be employed. The actuator provided at the proximal end will vary correspondingly. For example, where an electrical device at the distal end is used to move the element and release the stent, the actuator at the proximal end will include a switch or pair of contacts which can be connected to a switch or an external power source.

According to further variants, the movable element may be omitted if the stent itself will spontaneously release from the probe. For example, where the stent is a self-expanding type formed from a shape memory alloy as discussed above with reference to FIGS. 1–3, the movable element may be omitted. Also, if the stent will hook into a body structure upon advancing movement of the probe, the reverse movement of the probe can be used to disengage the probe from the stent, leaving the stent in position.

In the embodiments discussed above, the stent is placed within a structure of the vascular system. However, the stent may be placed in any tubular structure of the body, including the esophagus or other portion of the digestive tract or the airways of the respiratory system. If the stent is to be placed in the areas of the respiratory system while the patient is breathing normally, the system can be affected by so-called "motion artifact" which results as the thoracic tissues change size and shape during respiration. As disclosed in the copending, commonly assigned U.S. Patent Application of David E. Acker entitled, "Image-Guided Thoracic Therapy and Apparatus Therefore," filed of even date herewith, and as disclosed in U.S. Provisional Patent Application 60/038, 497, filed Feb. 25, 1997, the disclosures of which are hereby incorporated by reference herein, motion artifact caused by the movements due to respiration can be eliminated. The system can be operated to acquire the disposition of the probe distal end when the patient is in the same stage of the respiratory cycle that the patient was in during acquisition of the image. Other, more complicated expedients for suppressing motion artifact are also known.

Also, as described in the aforementioned PCT/US97/02335 application, a probe bearing a stent can be used in conjunction with another probe, referred to as a "site probe". The site probe may be placed within the body at a site near the location where the stent is to be placed, and the computer system may provide information representing the disposition of the stent-bearing probe relative to the site probe. For example, the site probe may include a balloon or other occluding device used to block flow through an artery during placement of the stent. The relative disposition information may be used to guide the stent-bearing probe into position. Alternatively, the stent-bearing probe may serve as the site probe, and a further probe may be guided to the stent placement site based on the relative disposition information.

According to yet another embodiment of the invention, the stent 336 (FIG. 6) may have a field transducer 350 mounted on it. Electrical leads 339 or other signal conductors such as fiber optics extend from the stent through the interior of probe 320 to the proximal end 324 of the probe, so that the signal conductors remain accessible outside of the patient's body during placement of the stent. The disposition of the stent can be monitored in the same way as discussed above during stent placement. The signal conductors may extend out of the body after placement or else may be embedded beneath the skin or in some other readily accessible location. Thus, transducer 350 can be used to determine the disposition of the stent. After placement, this capability can be used to locate the stent if it becomes dislodged, or to confirm that the stent remains in the correct position. Alternatively, the transducer-equipped stent may be utilized as a site probe in the methods as disclosed in the PCT/US97/02335 application, so that a further probe can be guided to the location of the stent based on the disposition of the further probe relative to the stent.

As these and other variations and combinations of the features discussed above can be utilized without departing from the present invention as defined by the claims, the foregoing description of the preferred embodiments to be taken by way of illustration rather than by way of limitation of the invention as defined in the claims.

I claim:

1. A method of applying a stent in a tubular structure within the body of a patient comprising the steps of:

(a) advancing a probe bearing a stent into the tubular body structure;

(b) determining a disposition of the stent relative to the patient, the determining step including the step of transmitting one or more non-ionizing fields to or from at least one internal field transducer on said probe or said stent, detecting each such transmitted field and deducing the disposition of the stent at least partially from the properties of said transmitted fields; and (c) releasing said stent from said probe when said determining step indicates that said stent is at a preselected disposition relative to said tubular structure.

2. A method as claimed in claim 1 wherein said determining step includes the step of determining the orientation of said stent relative to the patient's body.

3. A method as claimed in claim 1 wherein said tubular body structure includes a primary tube having a longitudinal axis, and wherein said step of determining the disposition of the stent includes the step of determining the orientation of the stent in roll about the longitudinal axis while the stent is at least partially positioned within said primary tube.

4. A method as claimed in claim 3 wherein said tubular structure includes a branch intersecting said primary tube, and wherein said stent includes a primary reinforcing element and a branch reinforcing element intersecting the primary reinforcing element, the method including the step of adjusting the orientation of the stent based upon the determined disposition of the stent so that the primary reinforcing element is disposed in said primary tube whereas the branch reinforcing element is disposed in said branch of said tubular element.

5. A method as claimed in claim 3 wherein said tubular structure includes a plurality of tubular branches intersecting said primary tube, and wherein said stent includes a primary reinforcing element and a plurality of branch reinforcing elements, the method including the step of adjusting the orientation of the stent based upon the determined disposition of the stent so that the primary reinforcing element is disposed in said primary tube whereas each branch reinforcing element is disposed in one of said tubular branches.

6. A method as claimed in claim 5 wherein said tubular structure is Y-shaped.

7. A method as claimed in claim 5 wherein said tubular structure is a structure of the vascular system or the respiratory system.

8. A method as claimed in claim 1 wherein said tubular structure is a structure of the vascular system, the digestive tract or the respiratory system.

9. A method as claimed in claim 1 wherein said step of determining the disposition of the stent relative to the patient includes the step of superposing a representation of the stent or the probe on an image of the patient.

10. A method as claimed in claim 9 wherein said determining step includes the step of transmitting said one or more fields between each said internal field transducer and one or more additional field transducers defining a locating frame of reference, determining the disposition of the probe in said locating frame of reference and transforming said disposition of said probe and said image into a common frame of reference.

11. A method as claimed in claim 10 wherein said one or more additional field transducers include at least one external field transducer mounted outside of the patient's body.

12. A method as claimed in claim 1 wherein said internal field transducer is mounted on said stent and said internal field transducer remains on the stent within the patient's body after the stent is released from the probe.

13. A method as claimed in claim 12 further comprising the step of determining the disposition of the stent after the stent had been released by transmitting one or more fields to or from said internal transducer.

* * * * *